US00PP23242P2

(12) United States Plant Patent
Danziger

(10) Patent No.: US PP23,242 P2
(45) Date of Patent: Dec. 4, 2012

(54) ***GAILLARDIA* PLANT NAMED 'DGAL901'**

(50) Latin Name: *Gaillardia pulchella*
Varietal Denomination: DGAL901

(75) Inventor: Gavriel Danziger, Moshav Mishmar Hashiva (IL)

(73) Assignee: Danziger 'DAN' Flower Farm (IL)

( * ) Notice: Subject to any disclaimer, the term of this patent is extended or adjusted under 35 U.S.C. 154(b) by 0 days.

(21) Appl. No.: 13/136,093

(22) Filed: Jul. 22, 2011

(51) Int. Cl.
*A01H 5/00* (2006.01)

(52) U.S. Cl. ..... Plt./431

(58) Field of Classification Search ..... Plt./431
See application file for complete search history.

*Primary Examiner* — Howard Locker
(74) *Attorney, Agent, or Firm* — Cassandra Bright

(57) ABSTRACT

A new and distinct *Gaillardia* cultivar named 'DGAL901' is disclosed, characterized by a somewhat compact plant habit, good branching and abundant flowering. The new variety begins blooming early in the season and flowers over a long period of time. The new variety is a *Gaillardia*, normally produced as an outdoor garden or container plant.

2 Drawing Sheets

Latin name of the genus and species: *Gaillardia pulchella.* Variety denomination: 'DGAL901'.

BACKGROUND OF THE INVENTION

The new *Gaillardia* cultivar is a product of a planned breeding program conducted by the inventor, Gavriel Danziger, in Moshav Mishmar Hashiva, Israel. The objective of the breeding program was to produce new *Gaillardia* varieties for ornamental commercial applications. The cross resulting in this new variety was made during April 2005.

The seed parent is the unpatented, proprietary seedling variety referred to as *Gaillardia pulchella* 'GAI-6-114' The pollen parent is unknown, as the crossing resulting in 'DGAL901' was an open pollination, with unidentifiable pollen parents. The new variety was discovered in July 2006 by the inventor in a group of seedlings resulting from the 2005 crossing, in a research greenhouse in Moshav Mishmar Hashiva, Israel.

Asexual reproduction of the new cultivar 'DGAL901' by vegetative cuttings was first performed at a research greenhouse in Moshav Mishmar Hashiva, Israel in February 2007 and has shown that the unique features of this cultivar are stable and reproduced true to type in successive generations.

SUMMARY OF THE INVENTION

The cultivar 'DGAL901' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DGAL901' These characteristics in combination distinguish 'DGAL901' as a new and distinct *Gaillardia* cultivar:

1. Somewhat compact habit
2. Highly floriferous
3. Long flowering season
4. Good branching
5. Early blooming Plants of the new cultivar 'DGAL901' are similar to plants of the seed parent, *Gaillardia pulchella* 'GAI-6-114' in most horticultural characteristics, however, plants of the new cultivar 'DGAL901' produce more flowers and branches on a more compact plant than 'GAI-6-114'.

COMMERCIAL COMPARISON

Plants of the new cultivar 'DGAL901' are comparable to the variety *Gaillardia* 'BALTORFLAM', U.S. Plant Pat. No. 16,125. The two *Gaillardia* varieties are similar in most horticultural characteristics, however, the new variety 'DGAL901' differs in having more flowers per plant, and a more upright plant habit.

Plants of the new cultivar 'DGAL901' can also be compared to the commercial variety *Gaillardia* 'BALTORYELL' U.S. Plant Pat. No. 15,966. These varieties are similar in most horticultural characteristics, however 'DGAL901' has a bi color flower, whereas 'BALTORYELL' is solid yellow. Additionally, 'DGAL901' has a different foliage form, more flowers per plant, and a more upright plant habit.

BRIEF DESCRIPTION OF THE PHOTOGRAPHS

Figure 1:
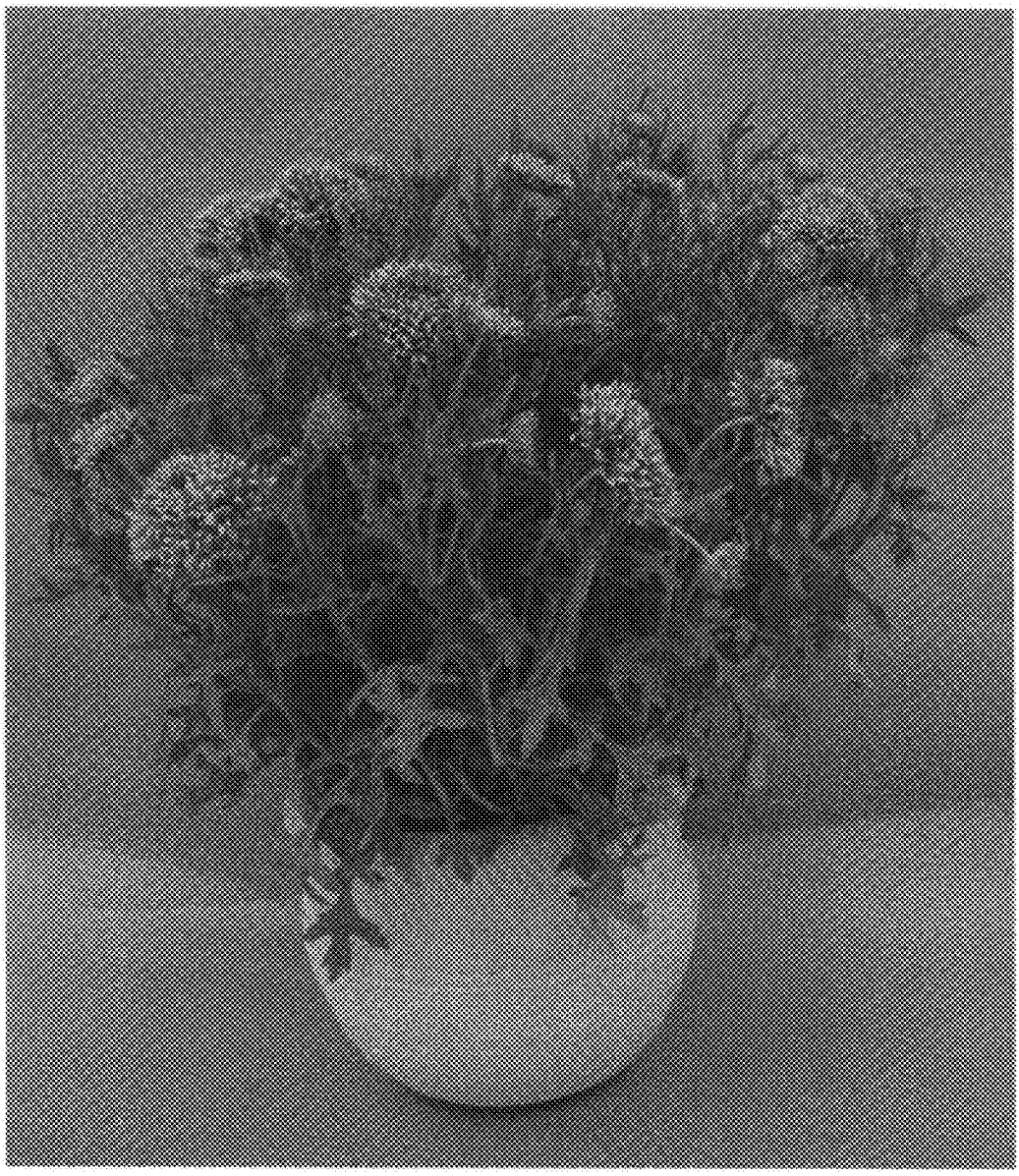

The accompanying photograph in FIG. 1 illustrates in full color a typical plant of 'DGAL901' grown in a greenhouse, in a 12 cm basket. Age of the plant photographed is approximately 8 weeks from a rooted cutting.

Figure 2:
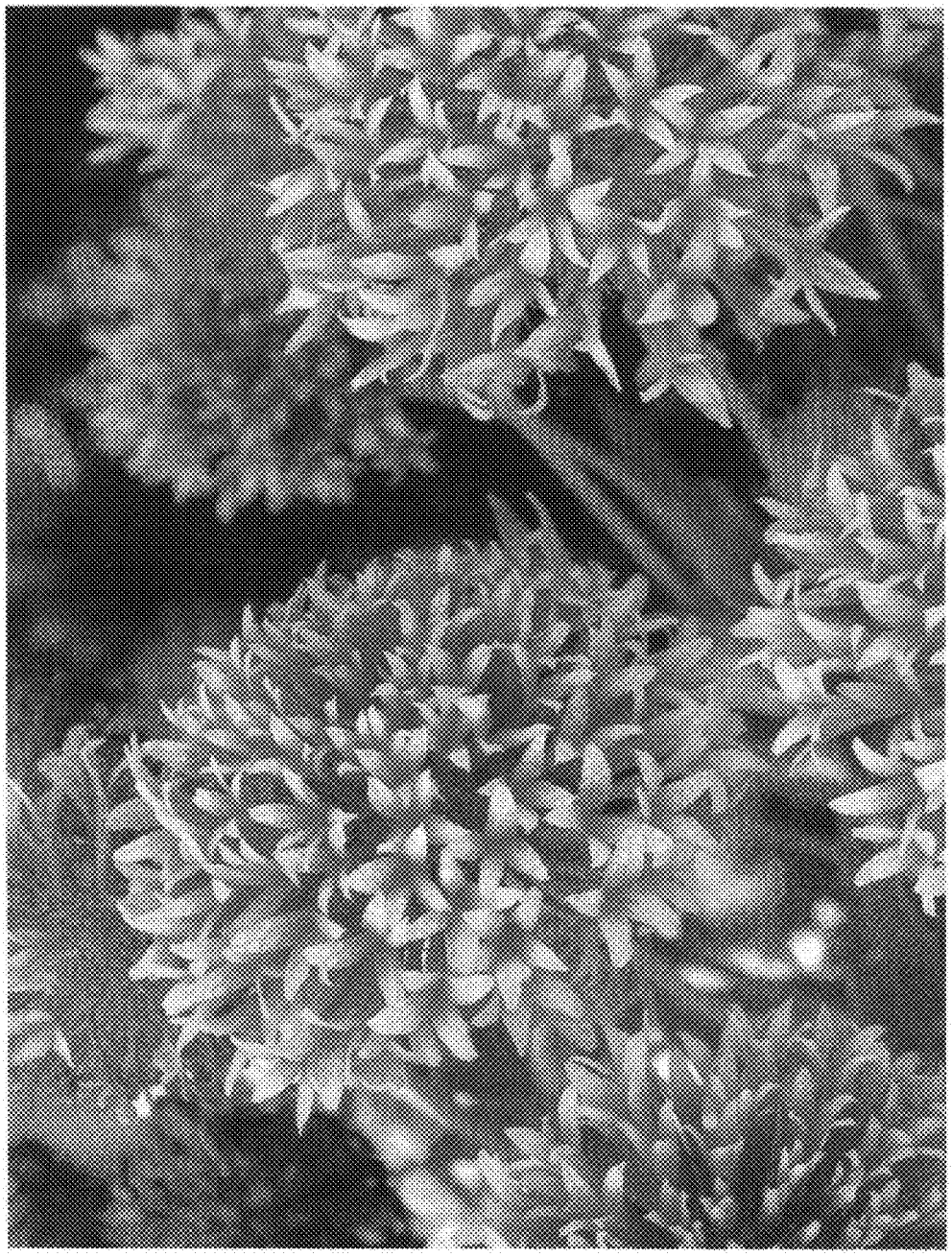

FIG. 2 illustrates in full color a close up of a typical bloom of 'DGAL901'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001 except where general terms of ordinary dictionary significance are used. The following observations and measurements describe 'DGAL901' plants grown outdoors during Spring in Moshav Mishmar Hashiva, Israel. The growing temperature ranged from 18° C. to 28° C. during the day and from 13° C. to 18° C. during the night. General light conditions are bright, normal sunlight. Measurements and numerical values represent averages of typical plant types. Plants are approximately 12 weeks old from a rooted cutting.

Botanical classification: *Gaillardia pulchella* 'DGAL901'.

PROPAGATION

Time to initiate roots: About 4 days at approximately 20° C.

Root description: Fleshy, well branched.

PLANT

Age of plant described: Approximately 60 days from a rooted cutting.

Growth habit: Compact, low growing and slightly spreading.

Pot size of plant described: 12 cm.

Height: Approximately 33 cm.

Plant spread: Approximately 45 cm.

Growth rate: Moderate.

Branching characteristics: Well Branched.

Length of primary lateral branches: Approximately 30 cm.

Quantity of primary lateral branches: Approximately 20.

Characteristics of primary lateral branches:

- *Form*.—Basal Branching.
- *Diameter*.—0.2 cm.
- *Color*.—Near RHS Yellow-Green 144C.
- *Texture*.—Densely covered with short bristly hairs.
- *Strength*.—Very strong.

Internodes length: Average 11 cm.

FOLIAGE

Leaf:

- *Shape*.—Pinnatisect.
- *Quantity*.—Approximately 12 per branch.
- *Average length*.—8 cm.
- *Average width*.—4 cm.
- *Apex*.—Rounded.
- *Base*.—Long attenuate.
- *Margin*.—Irregularly dentate.
- *Texture of top surface*.—Smooth.
- *Pubescence*.—None.
- *Aspect*.—45 degrees upwards.
- *Color*.—Young foliage upper side: Near RHS Green 137A. Young foliage under side: Near RHS Green 137B. Mature foliage upper side: Near RHS Green 137C. Mature foliage under side: Near RHS Green 137D.
- *Venation*.—Type: Pinnate. Venation color upper side: Near RHS Green 138B. Venation color under side: Near RHS Green 138B.
- *Petiole*.—Sessile.

FLOWER

Natural flowering season: March to August.

Days to flowering from rooted cutting.—6-7 weeks under ideal conditions.

Inflorescence and flower type and habit.—Solitary terminal capitulum, with nearly equal amounts of ray and disc floret.

Rate of flower opening.—3 to 5 days from bud to fully opened flower.

Flower longevity on plant.—5 to 7 days.

Persistent or self-cleaning: Self-cleaning.

Flower size:

- *Diameter of entire flower*.—Approximately 4 cm.
- *Depth of flower*.—Approximately 1.3 cm.
- *Disc diameter*.—Approximately 0.9 cm.
- *Receptacle shape*.—Rounded.
- *Receptacle height*.—Average 0.3 cm.
- *Receptacle diameter*.—Average 0.4 cm.
- *Receptacle color*.—Near RHS Green 137A.
- *Quantity of inflorescences per lateral stem*.—1.
- *Quantity of open inflorescences and buds per plant*.—Approximately 50.

Bud:

- *Shape*.—Flattened globular.
- *Length*.—0.9 cm.
- *Diameter*.—1.8 cm.
- *Color*.—Near RHS Yellow-Green 144A.

Ray florets:

- *Quantity*.—Young Flowers 80, Mature flowers 150 (Maturity is measured when the disc florets become fully opened).
- *Arrangement*.—Rotate, 3 rows.
- *Length*.—1 cm.
- *Width*.—0.8 cm.
- *Shape*.—Fan-Shaped.
- *Apex*.—Looking like 5 separate but fused petals.
- *Base*.—Fused into tubular shape.
- *Margin*.—Entire.
- *Texture, upper and lower surfaces*.—Smooth, slightly ribbed longwise.
- *Color*.—When opening, upper surface Main part of floret colored Near Red group N34A, N34B and N34C, and Yellow 14B at the tips. When opening, lower surface: Orange-Red N34A near center and Yellow 7B at the tips. Fully opened, upper surface: Main part of floret colored Near Red group N37C, N37B and N37A, and Yellow 14B at the tips. Fully opened, lower surface: Main part of floret colored Near Red N37C and Yellow 7C at the tips.

Disc florets: Disc Florets are fully open when flower is mature.

- *Quantity*.—Average 80.
- *Arrangement*.—Spirally placed on disc.
- *Length*.—1 cm.
- *Width*.—0.7 cm.
- *Shape*.—Trumpet Shape.
- *Apex*.—Acute.
- *Base*.—Fused.
- *Margin*.—Entire.
- *Texture, upper and lower surfaces*.—Smooth, Slightly glossy.
- *Color*.—When opening, upper surface: Main part of floret colored Near Red 46A and 53A and Yellow 2B at the tips. When opening, lower surface: Main part of floret colored Near Red 46A and 53A and Yellow 2B at the tips. Fully opened, upper surface: Main part of floret colored Near Orange-Red N34A, N34B and N34C, and Yellow-Orange 15C at the tips. Fully opened, lower surface: Main part of floret colored Near Orange-Red N34A and Yellow 14A at the tips.

Phyllaries/involucal bracts:

- *Quantity*.—Approximately 24.
- *Length*.—1.5 cm.
- *Width*.—0.3 cm.
- *Shape* (*overall*).—Lanceolate Ovate.

*Apex*.—Apiculate.
*Base*.—Truncate.
*Texture*.—Dull, covered with short hairs.
*Margin*.—Entire, with short hair directly on margin.
*Color*.—Near RHS Yellow-Green 147B.

Peduncles:
*Length*.—Average 8 cm.
*Diameter*.—0.2 cm.
*Angle*.—About 90° to the lateral branch.
*Strength*.—High.
*Texture*.—Slightly glossy.
*Color*.—Near RHS Yellow-Green 144A.

Fragrance: Slightly sweet scent.

REPRODUCTIVE ORGANS

Disc florets:
Stamens:
*Number*.—5.
Anthers:
*Shape*.—Connate.
*Length*.—Approximately 0.75 mm.
*Color*.—Near RHS Yellow-Orange 15A.
*Pollen*.—Present.
*Color*.—Near RHS Yellow-Orange 17A.
*Quantity*.—Moderate amount.
Pistil:
*Number*.—One present.
*Length*.—13 mm.
*Style*.—Length: 2 mm. Color: Near Yellow-Green 150D.
*Stigma*.—Shape: Bifid. Color: Near RHS Greyed-Purple 187A. Ovary Color: Near RHS Yellow-Green 150D.

Ray florets:
Stamens:
*Number*.—5.
Anthers:
*Shape*.—Connate.
*Length*.—Approximately 0.75 mm.
*Color*.—Near RHS Yellow-Orange 15A.
*Pollen*.—Near RHS Yellow-Orange 17B. Color: Near RHS Yellow-Orange 17A. Quantity: Moderate amount.
Pistil:
*Number*.—One present.
*Length*.—13 mm.
*Style*.—Length: 2 mm. Color: Near RHS Yellow-Green 150D.
*Stigma*.—Shape: Bifid. Color: Near RHS Greyed-Purple 187A. Ovary Color: Near RHS Yellow-Green 150D.

OTHER CHARACTERISTICS

Seeds and fruits: 50-70 seeds per flower, Shape—oblong tiangle, size—0.2 cm long×0.15 cm wide, with spine on top 0.3 cm long×0.2 wide.

Disease/pest resistance: Neither resistance nor susceptibility to pathogens and pests common to *Gaillardia* have been observed.

Temperature tolerance: The new variety exhibits a good temperature tolerance range for *Gaillardia*. Known tolerance for high temperatures to at least 35° C. Lower temperature tolerance unknown.

What is claimed is:

1. A new and distinct cultivar of *Gaillardia* plant named 'DGAL901' as herein illustrated and described.

* * * * *